US011207173B2

(12) United States Patent
Popescu

(10) Patent No.: US 11,207,173 B2
(45) Date of Patent: Dec. 28, 2021

(54) ADAPTIVE LOWER ESOPHAGUS SPHINCTER AUGMENTATION

(71) Applicant: Lucian Popescu, Houston, TX (US)

(72) Inventor: Lucian Popescu, Houston, TX (US)

( * ) Notice: Subject to any disclaimer, the term of this patent is extended or adjusted under 35 U.S.C. 154(b) by 178 days.

(21) Appl. No.: 16/561,077

(22) Filed: Sep. 5, 2019

(65) Prior Publication Data

US 2020/0078158 A1 Mar. 12, 2020

Related U.S. Application Data

(60) Provisional application No. 62/729,984, filed on Sep. 11, 2018.

(51) Int. Cl.
*A61F 2/04* (2013.01)
*A61F 2/08* (2006.01)
*A61F 2/48* (2006.01)

(52) U.S. Cl.
CPC .................. *A61F 2/04* (2013.01); *A61F 2/08* (2013.01); *A61F 2/482* (2021.08); *A61F 2002/044* (2013.01); *A61F 2002/0894* (2013.01); *A61F 2210/009* (2013.01); *A61F 2250/0001* (2013.01); *A61F 2250/0002* (2013.01)

(58) Field of Classification Search
CPC ............... A61F 2/04; A61F 2/08; A61D 1/16
USPC ........................................... 623/23.64–23.65
See application file for complete search history.

(56) References Cited

U.S. PATENT DOCUMENTS

| | | | |
|---|---|---|---|
| 10,568,630 B2* | 2/2020 | Hernandez | A61B 17/11 |
| 2005/0004425 A1* | 1/2005 | Banik | A61L 27/18 600/30 |
| 2005/0197715 A1* | 9/2005 | Kugler | A61B 17/0401 623/23.65 |
| 2009/0062825 A1* | 3/2009 | Pool | A61F 5/0059 606/157 |
| 2010/0076573 A1* | 3/2010 | Kugler | A61F 5/0069 623/23.64 |
| 2010/0274274 A1* | 10/2010 | Roslin | A61F 5/0043 606/192 |
| 2015/0196409 A1* | 7/2015 | Pool | A61F 5/0059 606/157 |
| 2016/0117951 A1* | 4/2016 | Fleischer | A61F 5/003 434/127 |
| 2017/0311897 A1* | 11/2017 | Faccioli | A61B 5/0004 |
| 2018/0185091 A1* | 7/2018 | Toth | A61N 1/303 |
| 2018/0243074 A1* | 8/2018 | Forsell | A61N 1/0507 |
| 2019/0000656 A1* | 1/2019 | Pool | A61F 5/0059 |
| 2019/0329042 A1* | 10/2019 | DiLorenzo | A61N 1/36189 |
| 2019/0374213 A1* | 12/2019 | Goldsmith | A61F 2/042 |
| 2020/0008299 A1* | 1/2020 | Tran | H05K 1/189 |
| 2020/0390328 A1* | 12/2020 | Toth | A61F 7/007 |
| 2021/0068839 A1* | 3/2021 | Shelton, IV | A61F 2/04 |
| 2021/0085210 A1* | 3/2021 | Duval | A61B 5/073 |

* cited by examiner

*Primary Examiner* — Suzette J Gherbi

(57) ABSTRACT

Apparatus consisting of a plurality of mechanically connected magnetic elements implanted around the lower esophagus sphincter with the purpose to restore its normal function in patients suffering from gastro-esophageal reflux disease (GERD), while avoiding dysphagia.

7 Claims, 12 Drawing Sheets

ADAPTIVE LOWER ESOPHAGUS SPHINCTER AUGMENTATION

CROSS-REFERENCE TO RELATED APPLICATIONS

Adaptive Magnetic Sphincter Augmentation (Application No. 62/729,984, filed on Sep. 11, 2018)

BACKGROUND OF THE INVENTION

This invention relates to human medical implants by way of surgical procedure. This novel solution's purpose is to restore a healthy lower esophagus sphincter (LES) function by preventing gastric reflux in gastro-esophageal reflux disease (GERD) patients, while improving the food swallowing process and avoiding patient dysphagia.

In chronically ill patients suffering from GERD, the LES has lost its normal strength preventing the stomach acid from flowing into the esophagus. If untreated, this condition can lead to severe deterioration of the esophagus' tissue lining from the presence of stomach acid in the esophagus, causing a painful burning sensation and triggering permanent structural modifications when normal esophagus' cells are replaced by abnormal (precancerous) cells (a medical condition called Barrett's esophagus). Furthermore, if left untreated, GERD increases the risk of developing esophageal adenocarcinoma, a serious, potentially fatal cancer of the esophagus.

GERD patients are most commonly treated with three classes of medications: antacids, H-2-receptor antagonists and proton pump inhibitors. None of these solutions address the GERD cause; they work instead to reduce the symptoms of acid reflux by partially neutralizing the acid in the stomach to alleviate its esophagus' "burning" effect. However, besides being ineffective in chronically ill GERD patients, some of these treatments interfere with a key role that stomach acid plays in protein digestion: the activation of digestive enzymes that break down the amino acids. Additionally, stomach acid helps the immune system by killing bacteria and parasites that are ingested with food. Another important benefit of maintaining a normal level of acid in the stomach is vitamin B12 absorption. Without adequate amounts of stomach acid, vitamin B12 stays bound to proteins and never becomes free to bind with other substances that carry it through the intestinal wall into the bloodstream. In order to address the above mentioned medications' shortcomings, surgical procedures are available. The most common antireflux surgery procedures are: Nissen Fundoplication and LINX®. Although antireflux surgery is considered both safe and effective, undesirable side effects can occur. The most common is long-lasting dysphagia (difficulty swallowing) after surgery. While they are fundamentally different (in Nissen Fundoplication, the upper part of the stomach is wrapped around the lower end of the esophagus, while the LINX® procedure implants a flexible band of magnet beads around the LES), both surgical procedures constrict the LES passage with the purpose of preventing stomach acid from flowing up into the esophagus. This increases the LES strength and is effective in addressing the acid reflux problem, but it also makes the food swallowing process more difficult, potentially triggering a permanent condition called dysphagia. As a result, food pooling in the lower part of the esophagus can occur. In these instances, regurgitation (voluntary or involuntary) is often the only method to clear the esophagus pathway. Besides the pain and discomfort, these situations may pose significant issues which greatly affect the patient's quality of life. In addition to creating potentially embarrassing situations, these episodes may escalate in much more serious health problems that could become life threatening: a patient may choke on food accidentally penetrating into the trachea and blocking the airway into the lungs. These occurrences (E.g. LINX® generated dysphagia) are well documented in the medical literature and internet public domain. Variants of Nissen Fundoplication procedure (which is sometimes called complete fundoplication because the stomach fundus is wrapped 360 degrees around the esophagus) try to address the dysphagia by only partially wrapping the stomach lining around the LES. However, although this alleviates the dysphagia symptoms, it is less effective in preventing stomach acid from flowing into the esophagus. Finally, it is important to mention another deficiency of the LINX® procedure, which is the LINX® band's limited capability to expand. As a result, after a patient has had the LINX® implant placed around their LES, if they do not thoroughly chew their food before swallowing, the food bolus may not pass through the LES into the stomach.

BRIEF SUMMARY OF THE INVENTION

The Adaptive Lower Esophagus Sphincter Augmentation (ALESA) novel solution is designed to restore a healthy lower esophagus sphincter's function, preventing gastric reflux in GERD patients, while improving the food swallowing process and avoiding patient dysphagia.

ALESA is a device which uses a specific combination of Permanent Magnets (PM) and Electromagnets (EM) that is assembled in a ring configuration and is surgically implanted around the LES in the abdominal cavity, in the proximity of the esophageal hiatus. The ALESA device helps the LES stay closed by means of a magnetic attraction force generated by the PM elements of the magnetic assembly if no food passes through the LES. However, when the human subject initiates the swallowing process, the ALESA detects the food bolus approaching the LES and opens the magnetic assembly by temporarily cancelling or weakening the magnetic force that keeps the ALESA magnetic assembly contracted. Due to this temporary cancellation or weakening of the magnetic attraction force, the food bolus advances easily through the LES. This allows the PM-EM ring to expand under the positive pressure developed by the esophageal muscles during the swallowing process. An expanded (opened) ring has a lower magnetic force attraction, making it easier for food to advance into the stomach; hence the patient does not have to develop a persistent and painful high pressure in the esophagus. After food passes through the LES into the stomach, the ALESA magnetic assembly ring closes back until a new swallowing is initiated.

The temporary cancellation/weakening of the magnetic force in the ALESA magnetic assembly ring can be achieved by circulating an electric current into the EM copper wire windings and subsequently developing a magnetic field which opposes the one continuously generated by the PM elements. By temporary relieving the magnetic force that keeps the ALESA magnetic assembly ring tightly closed around the LES, the patient has an improved and painless swallowing experience. The ALESA design closely emulates the natural function of a healthy LES, which relaxes the sphincter muscle during food swallowing and esophageal advancement and closes tightly after the process is complete.

DETAILED DESCRIPTION OF THE INVENTION

Figure 1:
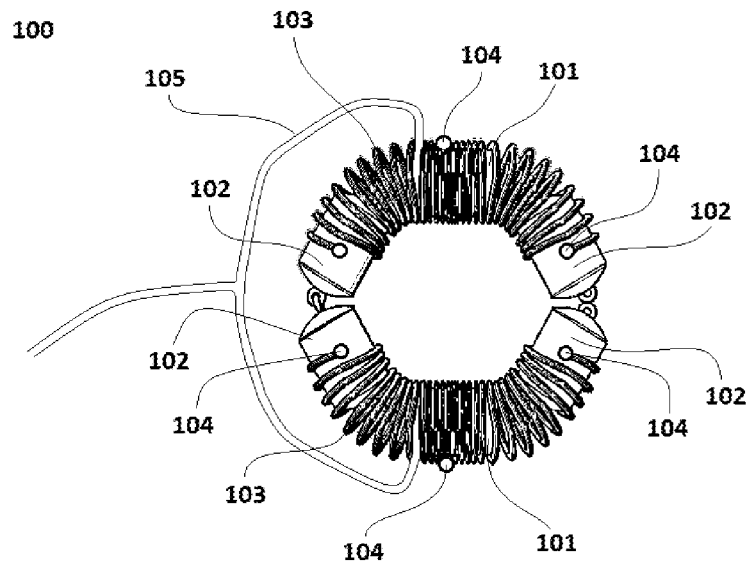
FIG. 1 illustrates a top view of the ALESA magnetic assembly in a contracted ring configuration state.
Figure 3:
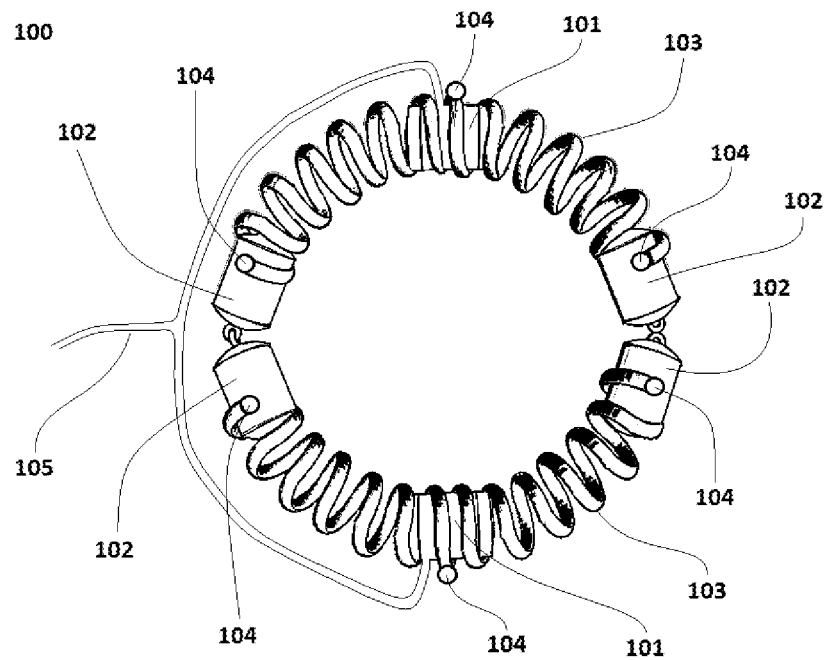
FIG. 3 depicts a top view of the magnetic assembly in an expanded ring configuration state.
Figure 7:
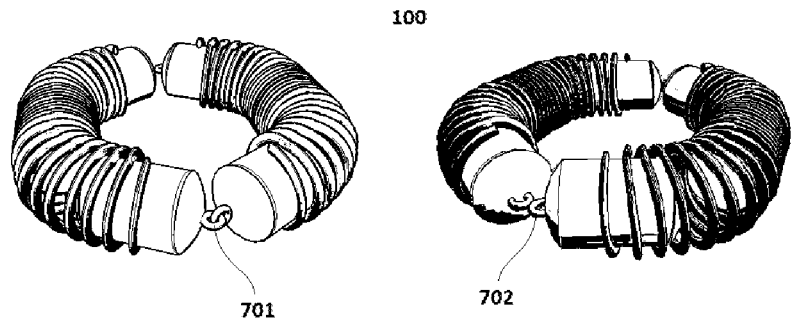
FIG. 7 shows two opposite side views of the magnetic assembly, in a contracted ring configuration state, showing the PM-PM elements connection details.
Figure 8:
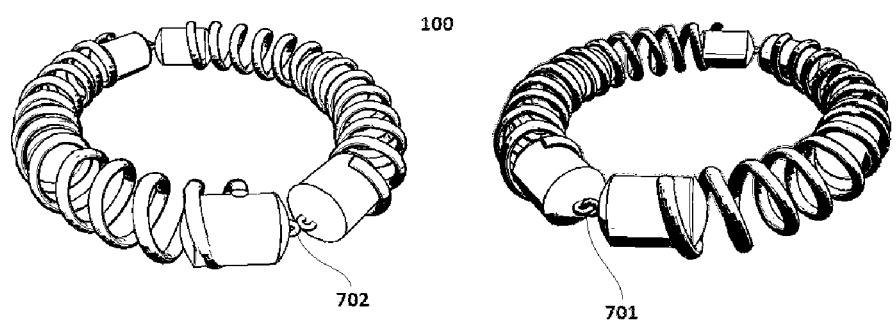
FIG. 8 illustrates similar side views as FIG. 7 but shows the magnetic assembly in an expanded ring configuration.

Magnetic assembly 100 is the main component of the ALESA apparatus and consists in a plurality of EM elements 101 and a plurality of PM elements 102, alternating and mechanically connected together as seen in FIG. 1, FIG. 3, FIG. 7, FIG. 8 and FIG. 9. More specifically, FIG. 1 and FIG. 3 show a top view, while FIG. 7 and FIG. 8 show a side view of the preferred embodiment of the mechanical attachment apparatus in a ring configuration. It is mechanically designed to fully contract (see FIG. 1 and FIG. 7) and expand (see FIG. 3 and FIG. 8), to allow the magnetic assembly string of EM and PM elements to change diameter when mounted around the LES in a ring configuration.

Figure 5:
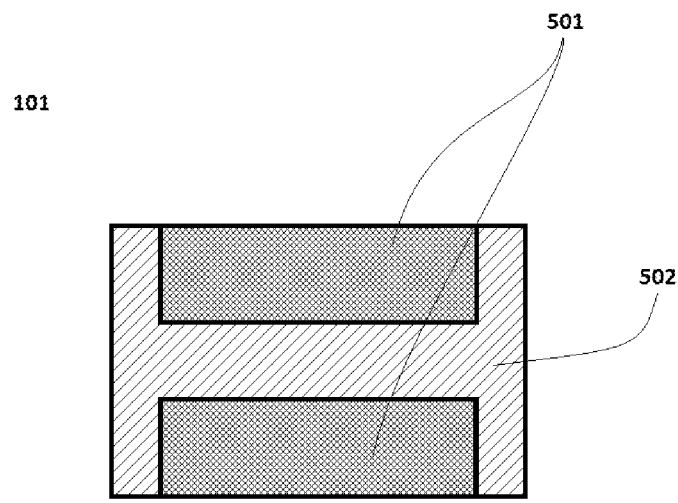
FIG. 5 details a sectional view of the EM element.
Figure 10:
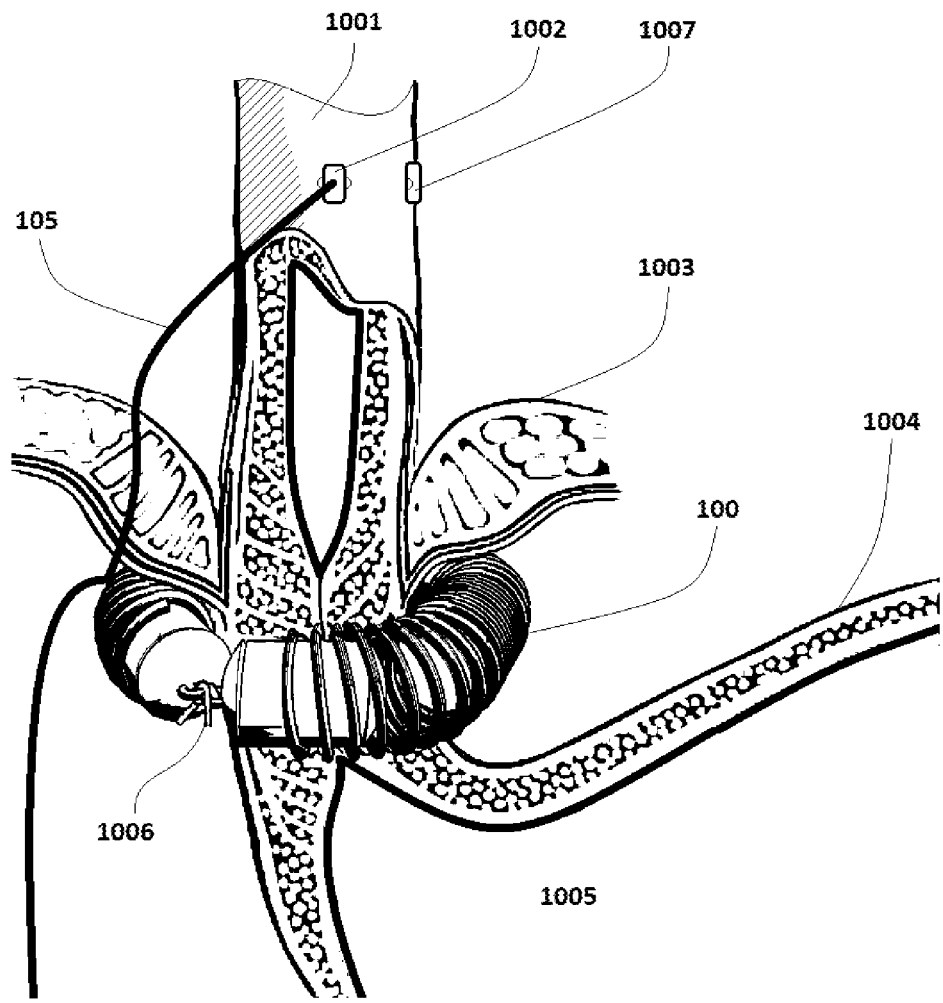
FIG. 10 is a view showing a partial cross-section of the esophagus and stomach, with the magnetic assembly mounted around the LES. This figure illustrates the area of the lower esophagus where it meets the stomach, after magnetic assembly is mounted around the LES in a resting state. In this state, the magnetic assembly is contracted, preventing the stomach contents from flowing into the esophagus.
Figure 11:
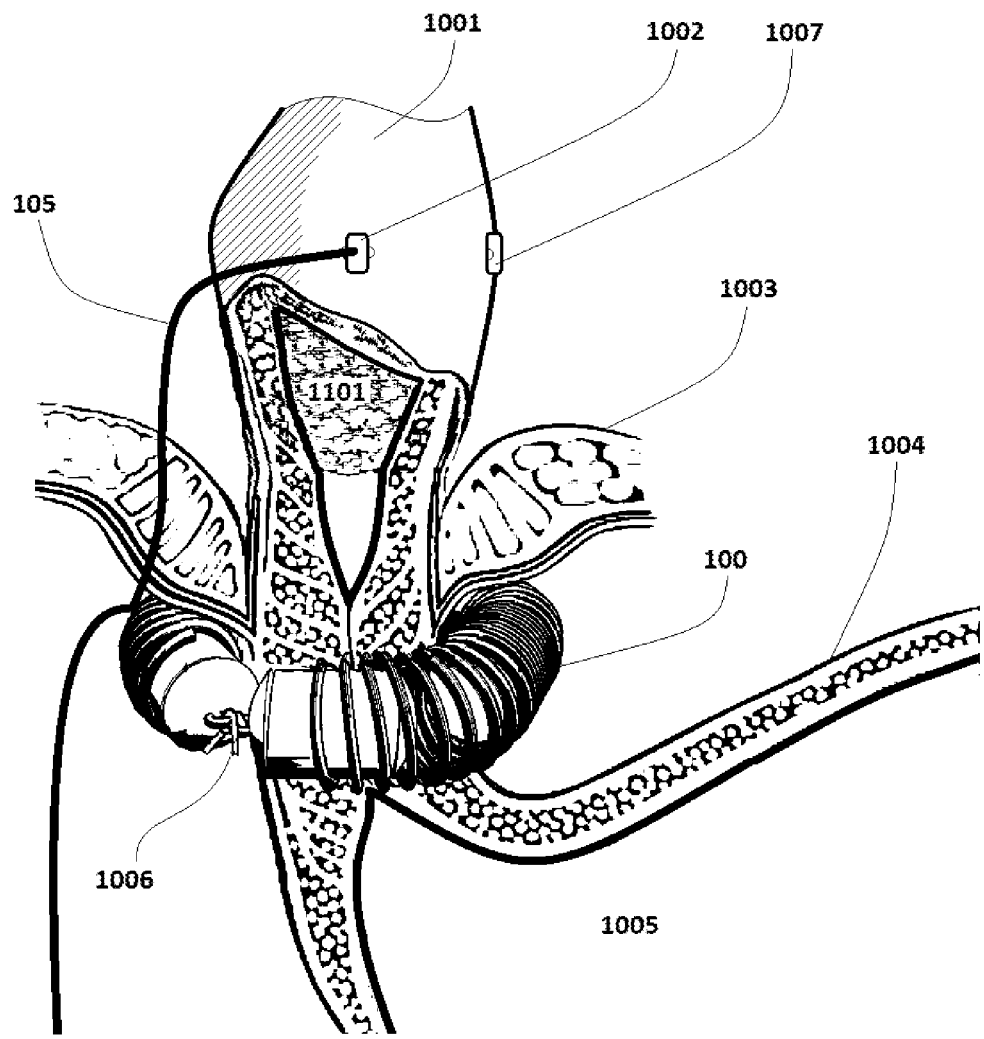
FIG. 11 is a partial sectional view of the esophagus and stomach, with the magnetic assembly mounted around the LES, showing the food bolus approaching the LES during the food swallowing process. Magnetic assembly is still contracted and prevents the stomach contents from flowing into the esophagus.
Figure 12:
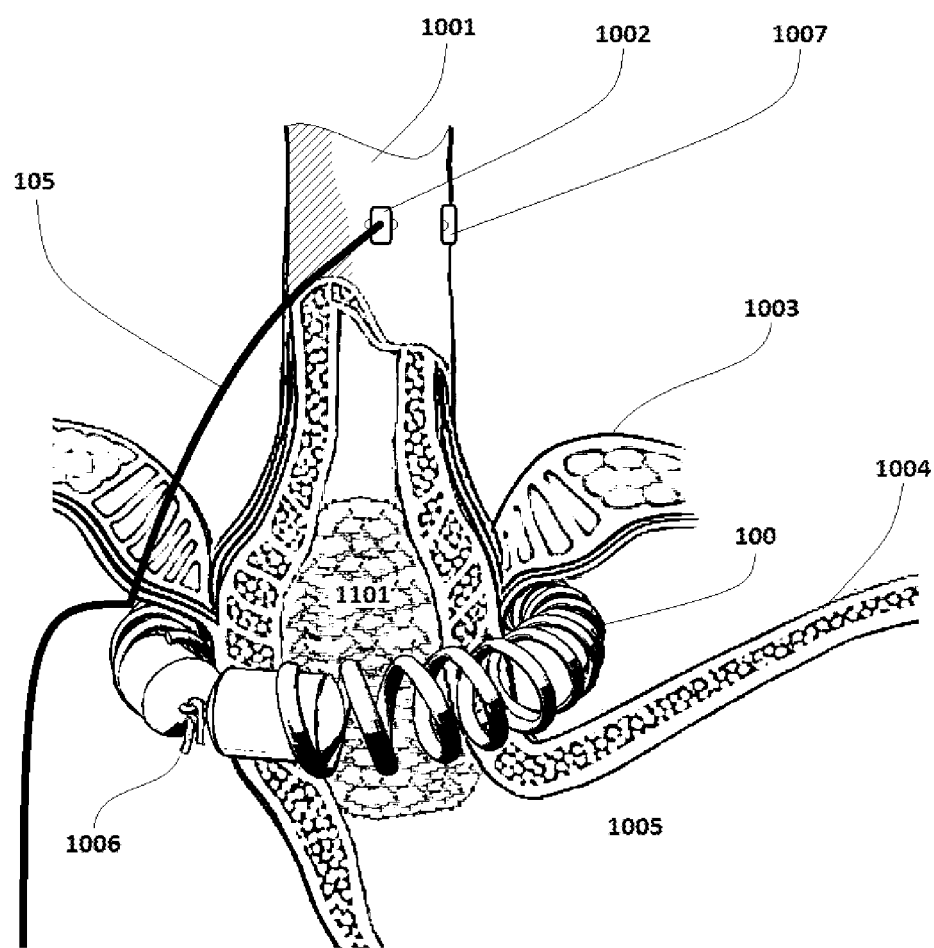
FIG. 12 is a partial sectional view of the esophagus and stomach, with the magnetic assembly mounted around the LES, showing the food bolus reaching the LES during the food swallowing process. Magnetic assembly is expanded, allowing the food bolus to freely advance into the stomach.
Figure 15:
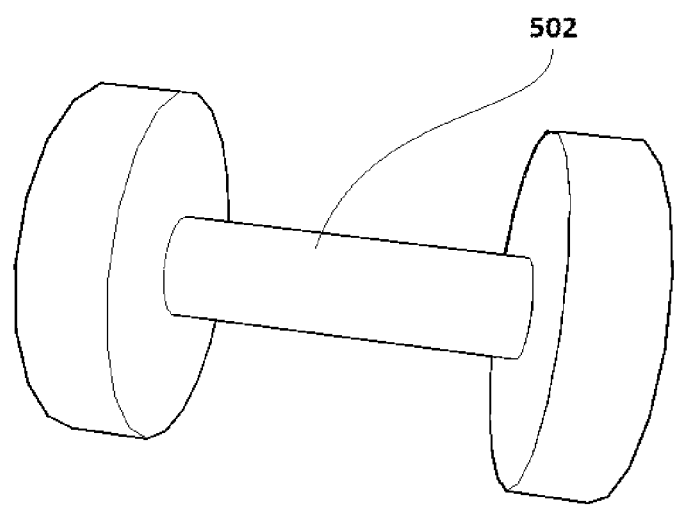
FIG. 15 is a detailed view of the high magnetic permeability core used in building the EM element.
Figure 17:
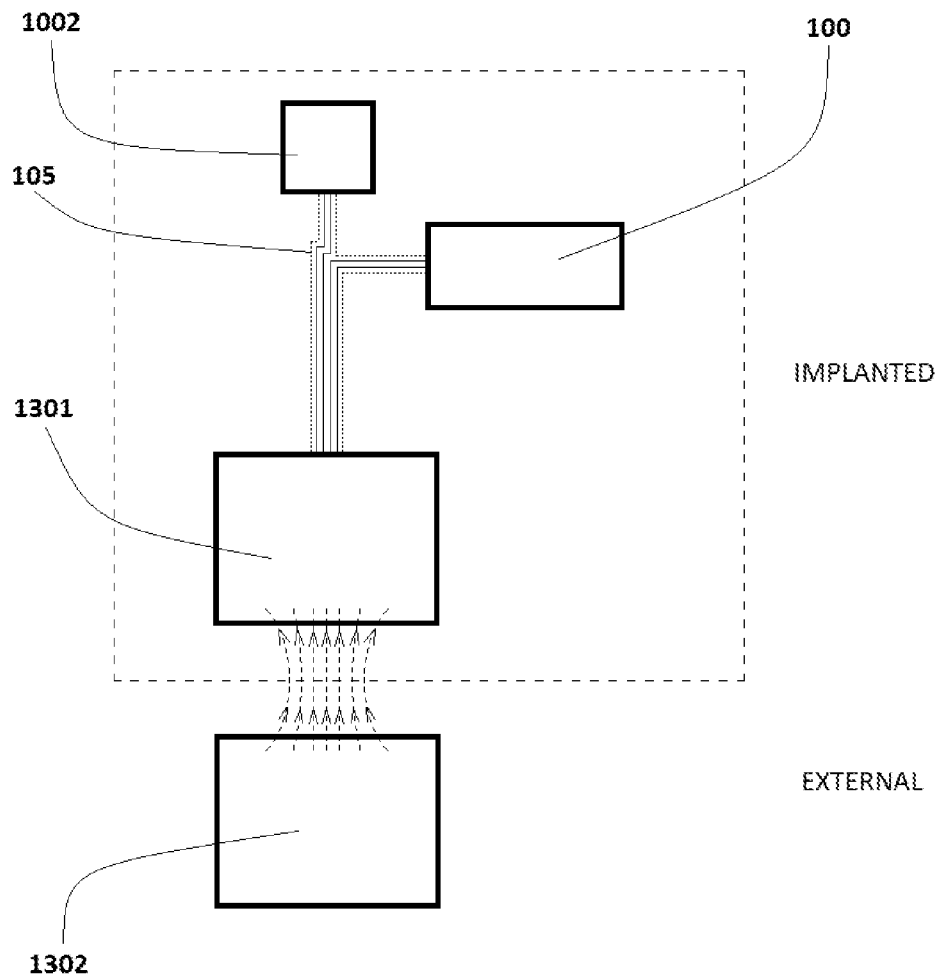
FIG. 17 is an electrical diagram showing how various modules of the ALESA apparatus connect together.

As explained in the previous paragraph, EM elements 101 are main components of the magnetic assembly 100. FIG. 5 shows a sectional view of the EM element 101. Item 502 represents the EM element's high magnetic permeability core that may be made out of pure iron or Metglas alloy as an example. However, it is understood that somebody skilled in the art may use many other high magnetic permeability materials without departing from the scope of this invention. For a better understanding of the EM's core manufacturing process, a separate view of item 502 is shown in FIG. 15. The high magnetic permeability core 502 is furthermore used as a "bobbin" to provide the mechanical support around which a very thin, electrically isolated copper wire (also called magnet wire or enameled wire) is utilized to construct a substantial wire winding, typically consisting of hundreds of turns, wound in the same direction, shown as item 501 in the sectional view pictured in FIG. 5. Although it is not illustrated in FIG. 5, it is understood that the copper wire's beginning and end terminations are extended significantly and are bundled together, passing through a flexible, tiny but mechanically reliable tube sleeve made out of implantable-grade polymer materials to create an electric cable 105, long enough to comfortably reach the other electrical modules of the ALESA apparatus. The purpose of this cable is to seal and mechanically protect the EM element's wire extensions and prevent their rupture. As shown in FIG. 1 and FIG. 3, this electric cable 105 merges with a similar cable originating from the second EM element. Moreover, electric cable 105 mechanically merges with the food bolus' detection sensor's 1002 own cable, as shown in FIG. 10, FIG. 11 and FIG. 12. Finally, all these merged cables are routed to the control & power unit (item 1301) pictured in FIG. 13, per the electrical connection diagram of FIG. 17. In the end, it needs to be emphasized that the whole EM element must be sealed and enclosed in a case made of an implantable-grade material such as, but not limited to, titanium or biocompatible polyethylenes. It is important to state that these materials must have non-magnetic properties.

Figure 6:
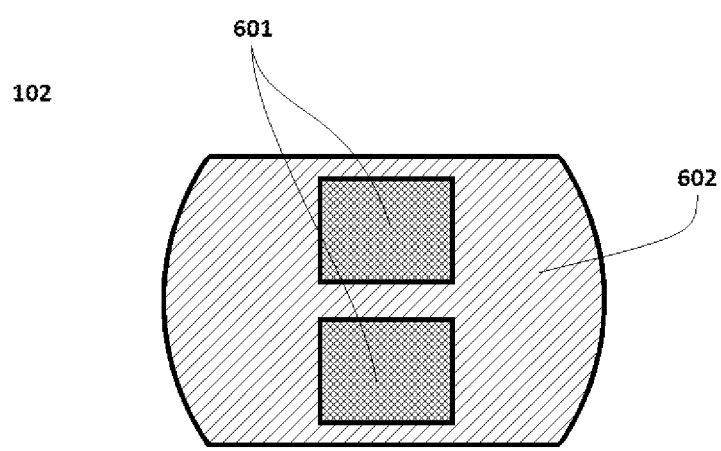
FIG. 6 details a sectional view of the PM element.
Figure 16:
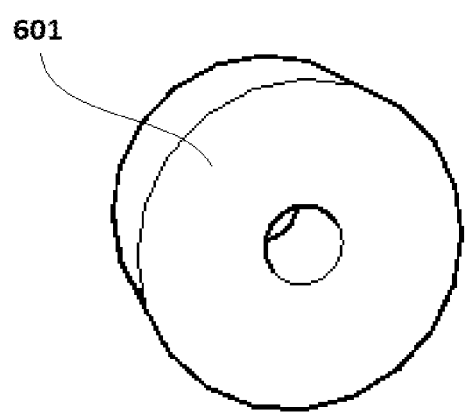
FIG. 16 is a detailed view of the permanent magnet used in building the PM element.

Other important components of the magnetic assembly 100 are the PM elements 102. A sectional view of a PM element 102 is shown in FIG. 6. Item 601 represents a strong permanent magnet made out of neodymium or a similar rare-earth magnet material. A detailed view of item 601 is pictured in FIG. 16. Item 602 in FIG. 6 shows a filling non-magnetic material; its purpose is to achieve the mechanical strength and dimensions of the PM element 102 without contributing to or disturbing the magnetic field generated by the permanent magnet 601. Finally, in a similar way as was mentioned in the previous paragraph, the PM element 102 must be sealed and enclosed in a case made of an implantable-grade material such as, but not limited to, titanium or biocompatible polyethylenes. It is again important to state that this material must have non-magnetic properties.

Figure 2:
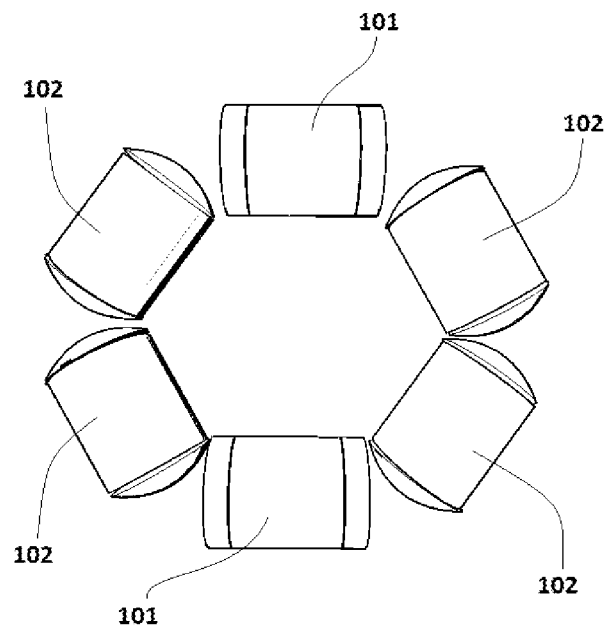
FIG. 2 shows a top view of the same representation of magnetic assembly ring as in FIG. 1, picturing only its essential EM and PM elements.
Figure 4:
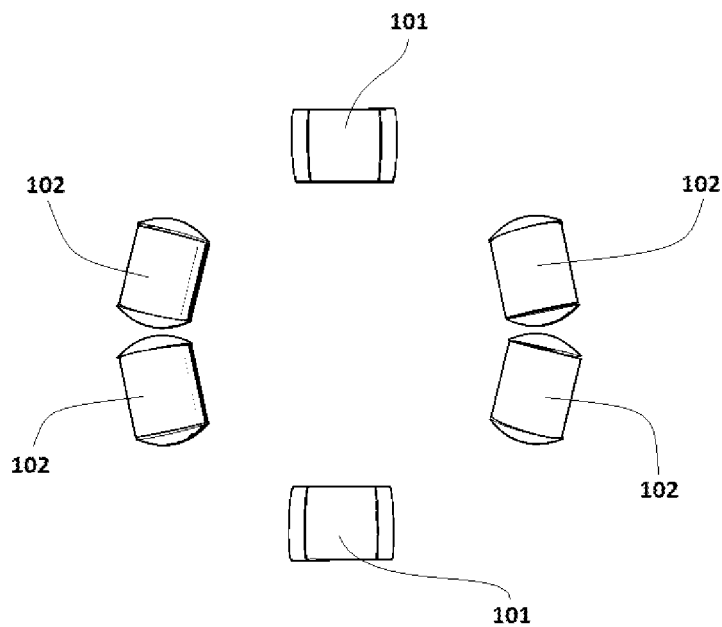
FIG. 4 represents a top view of the same representation of magnetic assembly ring as in FIG. 3, picturing only its essential EM and PM elements.
Figure 9:
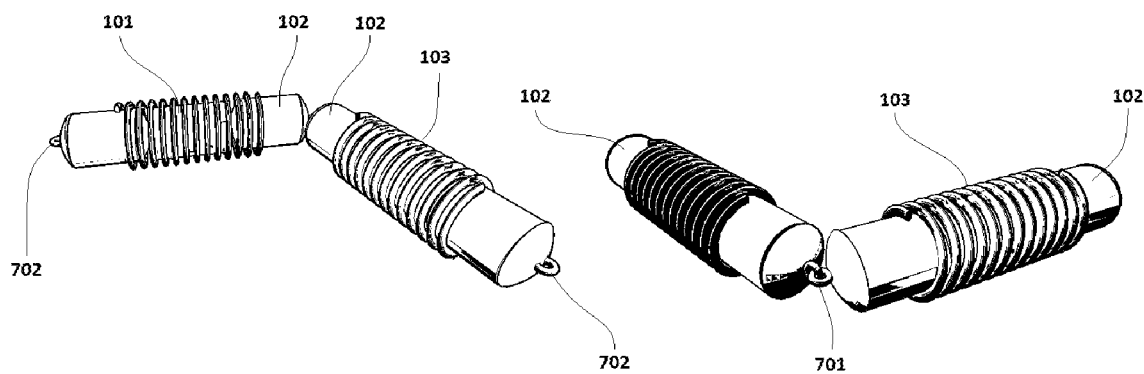
FIG. 9 shows two opposite side views of the magnetic assembly in its natural resting and contracted position before being implanted via surgical procedure.

The EM and PM elements are assembled together in a specific order so they can accomplish the desired function of the ALESA apparatus: when implanted around the LES in a ring configuration, to have the ability of significantly modifying its diameter so as to prevent stomach acid from flowing into the esophagus (when the magnetic assembly 100 is fully contracted) and allow the food bolus 1101 to easily pass through the LES into stomach (when the magnetic ring is in an expanded state). FIG. 9 shows two opposite views of the magnetic assembly 100 in a relaxed, not implanted state. FIG. 9 shows only the EM and PM elements, the spring coils and the links that keep them together. For simplicity, FIG. 9 does not illustrate the complete details of the magnetic assembly 100. For example, it does not show the EM wires bundle which electrically connects the two EM elements 101 together, as well as the other functional modules of the ALESA apparatus, as it will be explained in the following paragraphs. It can be observed in FIG. 9 that a preferred embodiment of magnetic assembly 100 is built out of two identical string configurations, permanently attached together by circular links 701. Next will be explained how an individual string of the preferred embodiment is constructed: the first component of the string is a PM element 102. This first PM element has a circular link 702 welded to its end. Next component of the string is an EM element 101, followed by another PM element 102. This last PM element is terminated with another circular link 701 welded to the PM's external case. On the other hand, the three elements (PM-EM-PM) are mechanically attached together by means of a spring coil 103 that wraps around them as seen in FIG. 1, FIG. 3, FIG. 7, FIG. 8 or FIG. 9. The spring coil 103 is made out of titanium or an equivalent material having permanent elastic properties. Furthermore, FIG. 1 and FIG. 3 show the welding points 104 between the spring coil 103 and the three PM-EM-PM elements' external cases, permanently attaching them to the spring coil. Finally, it is important to mention that the two identical PM-EM-PM strings are pre-attached via the two circular links 701 in a chain configuration, providing the assembly with the necessary mechanical flexibility. The remaining two open links 702 at the beginning and the end of the magnetic assembly 100 are secured together by a suture knot 1006 when implanting the magnetic assembly 100 around the LES. For a better understanding of how the EM and PM elements are positioned relative to each other when item 100 is implanted around the LES, FIG. 2 shows only the EM and PM elements when item 100 is in a constricted state, while FIG. 4 shows only the EM and PM elements when item 100 is in an expanded state. It is important to mention that additional and alternating EM and PM elements can be inserted to the preferred embodiment of magnetic assembly 100 described above, without departing from the teachings of this invention. It is also important to mention that since various patients are expected to have slightly different diameters of the esophagus, a range of diverse dimensions for the magnetic assembly 100 must be made available for optimal fitting around the patients' LES. However, this collection of magnetic assemblies 100 having slightly different dimensions must be designed in such a way as to possess identical magnetic properties.

Figure 13:
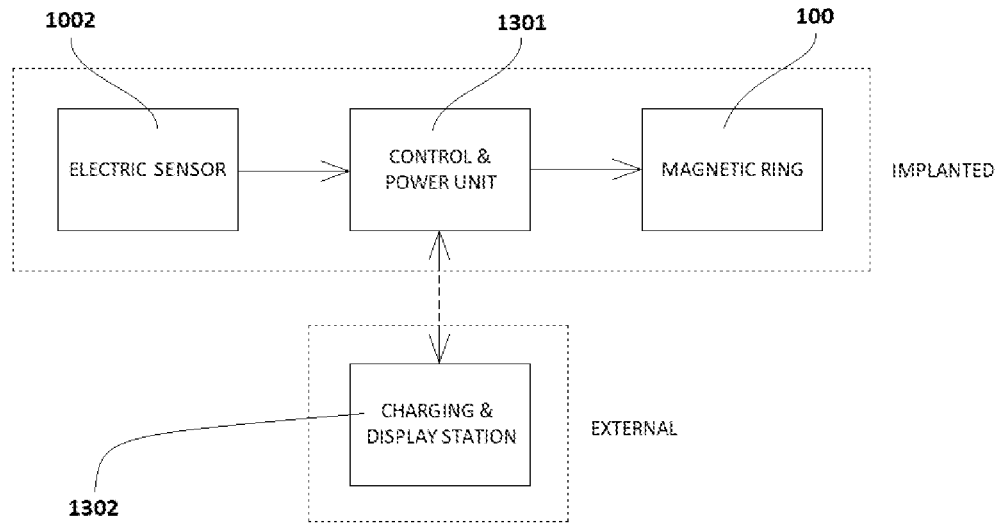
FIG. 13 is a diagram showing the functional blocks of the complete ALESA apparatus.
Figure 14:
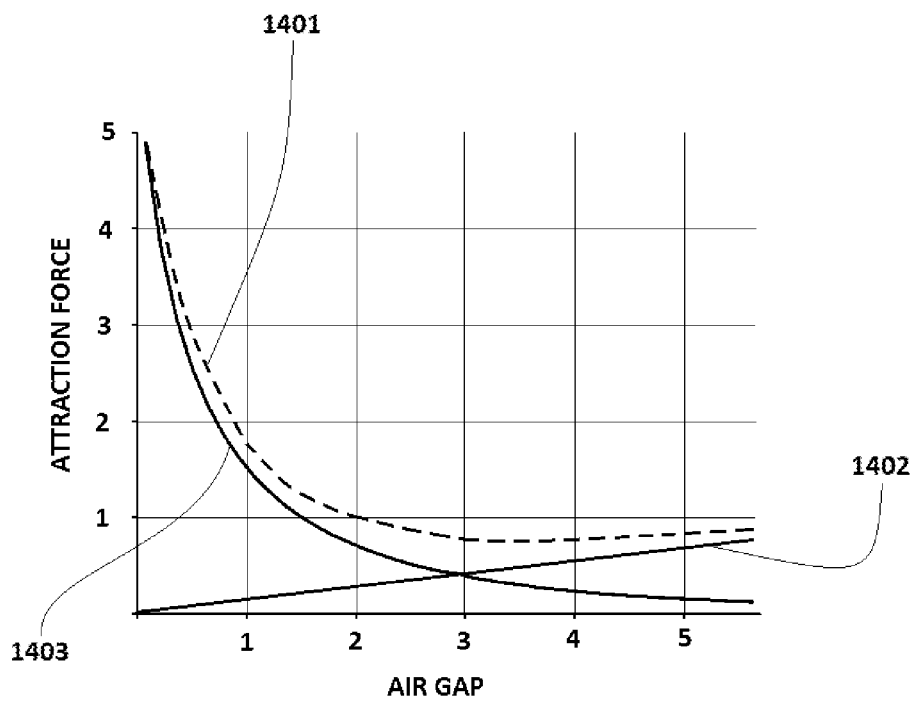
FIG. 14 is a graphical representation depicting the attraction force generated by the magnetic assembly ring elements versus the air gap (distance between the said elements). It is understood that the horizontal and vertical axes' units are generic and for illustration purpose only; they do not represent specific values.

Per block diagram illustrated in FIG. 13, the ALESA apparatus consists in functional modules that are implanted in the patient's body such as magnetic assembly 100, control & power unit 1301, food bolus' detection sensor 1002, and external modules such as the charging & display station 1302. FIG. 10, FIG. 11 and FIG. 12 show where some of the ALESA's apparatus implanted modules must be positioned in the human body, and how they interact to accomplish the ALESA apparatus' intended purpose. As was already stated, the magnetic assembly 100 shall be implanted in the abdominal cavity, mounted around the LES with the main function of keeping the esophagus closed by means of a magnetic attraction force generated by the PM elements. In its resting state, when mounted around the LES and not powered by the electric battery located in item 1301, the magnetic assembly 100 must be specifically engineered to develop a sufficiently strong magnetic attraction force to prevent the stomach acid from flowing into the esophagus. However, this attraction force which keeps the magnetic assembly 100 in a contracted state around the LES, must not be too great as to cause necrotic pressure on any tissue of the esophagus or to prevent stomach venting when necessary. Item 100's magnetic attraction force is achieved by the specific orientation of the PM elements, arranged in such a way so they each develop individual magnetic field lines having the same direction. The resulting common magnetic field lines are adding and concentrating inside the ferromagnetic (high magnetic permeability) core of the EM elements, hence the resulting attraction force between the magnetic assembly's PM and EM elements. When a swallowing is initiated by the patient implanted with the ALESA apparatus, and food bolus 1101 advances down the esophagus approaching the LES, as shown in FIG. 11, the food bolus' detection sensor 1002 will notice the temporary expansion of the esophagus wall tissue and will send a feedback electric signal to the item 1301 via electric cable 105. In a preferred embodiment, the food bolus' detection sensor 1002 can be a magnetic reed switch, normally open, that shall detect the relative movement of a small permanent magnet 1007. Both item 1002 and item 1007 are conveniently attached to the esophagus wall tissue during the implant surgery procedure. Suture may be used to secure item 1002 and item 1007 to the desired position on the outer surface of the esophagus. It is well understood from the teachings of this invention that item 1002 can be any type of sensor that would accomplish the food bolus detection function. When food bolus' detection sensor 1002 sends an electrical signal (which can be a switch status change in the preferred embodiment explained above) to item 1301, said item 1301 will immediately and reliably energize the magnetic assembly's EM elements. The process of energizing the magnetic assembly's EM elements is accomplished by circulating a current pulse through the EM elements' wire windings. The current pulse will typically last 250 ms to 500 ms and will be sufficiently strong to generate a counter-magnetic field that temporary cancels or weakens the permanent magnetic field produced by the PM elements. Therefore, the magnetic assembly's attraction force is temporary cancelled. It is obvious for somebody skilled in the art relevant to this invention, that the EM elements' orientation, electric current direction and electric current strength, circulating through their wire windings must be specifically designed to accomplish the magnetic force cancellation or weakening. As a result of item 100 magnetic attraction force's temporary cancellation, the food bolus 1101 will easily advance through the LES as can be observed in FIG. 12, while item 100 expands as much as necessary to accommodate the food bolus size. It must be noted that since the magnetic ring's EM and PM elements relative distance will substantially increase during the food bolus advancement through the LES, the attraction force will never decrease under a certain threshold. This force strength threshold is substantially lower than the magnetic force generated by the PM elements when item 100 is resting in a fully contracted state. Although the magnetic attraction force decreases with the square of the distance between the PM elements (shown as item 1403 in FIG. 14), the spring coil mechanism keeping the PM-EM-PM elements of the magnetic string together will develop an independent attraction force (elastic force) that proportionally increases with the distance between the PM-EM-PM elements (pictured as item 1402 in FIG. 14). This elastic attraction force will combine with the magnetic attraction force and will assure that the PM-EM elements of item 100 will always be brought back together so the magnetic assembly ring goes back to a contracted position around the LES. This is particularly important after the circulating electric current through the EM elements' wire windings decays to zero. The combined attraction force of item 100 due to the PM elements (magnetic force) and spring coils (elastic force) is pictured as a dashed line in FIG. 14 (item 1401).

Figure 18:
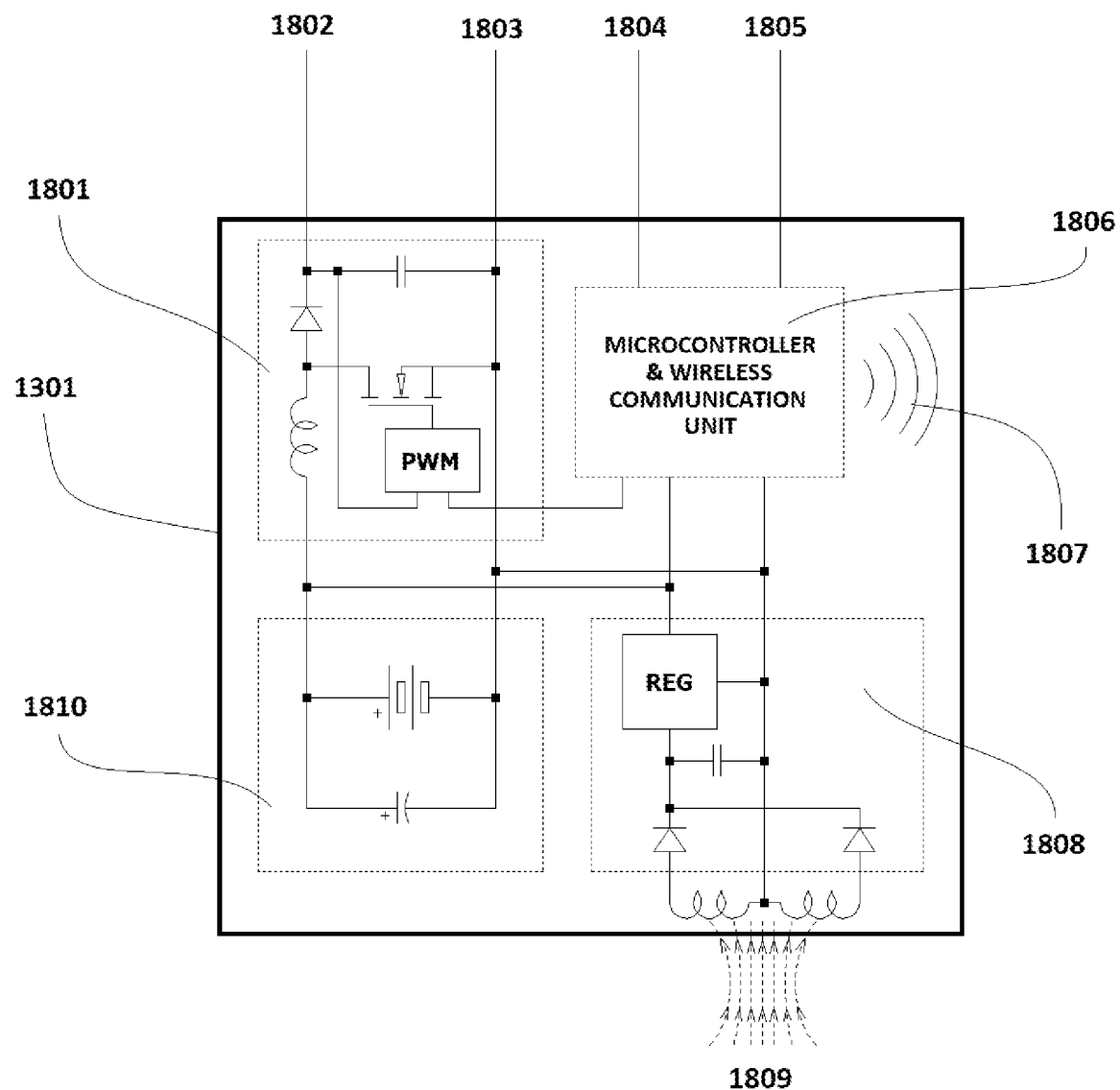
FIG. 18 is a block diagram of the Control & Power Unit (CPU).

FIG. 18 shows the internal block diagram of the control & power unit (item 1301). As explained in the previous paragraph, the energy to temporarily demagnetize the ALESA magnetic assembly ring (item 100) comes from the rechargeable battery 1810, located in the control & power unit. In a preferred embodiment, the rechargeable battery can be an implantable-grade lithium-ion rechargeable battery. The control & power unit 1301 must be sufficiently small and flat in shape and can be conveniently implanted under the skin, in the abdominal area of the patient. Typically, the battery can be recharged once every 2-3 days, with the recharging cycle decreasing to once per day towards the end of the battery life. Normally, the battery module 1810 should last between 7 to 10 years before replacement through surgical procedure should be considered. For convenience, when battery replacement is necessary, the whole item 1301 shall be replaced. The battery charging process is accomplished via a wireless charger. Typically, a battery can be charged to 70% of its full capacity in about 15 minutes and, as stated above should last 2-3 days when the battery is new. It must be noted that lithium-ion batteries do not need to be fully charged to be functional. Partial charging does not negatively affect battery life and charging process can be interrupted and resumed whenever is convenient to the patient without negative consequences to battery life. Although lithium-ion technology rechargeable battery is preferred, it is understood that any type of rechargeable battery that accomplishes the energy storage function of the ALESA apparatus can be utilized without departing from the teachings of this invention. As explained above in this paragraph, the battery shall be charged via a wireless charger. To achieve its function, the wireless charger has two elements: the transmitter element 1902 which is external and is part of the charging & display station 1302, and the receiver element 1808 which is part of the control & power unit 1301. The latter element 1301, as it was explained above in this paragraph, shall be implanted under the skin in the patient's abdominal area. In a preferred embodiment, the wireless charger can transfer power from transmitter to receiver using near-filed (nonradiative) techniques, and more specifically using resonant or non-resonant inductive coupling of magnetic fields. In another proposed embodiment, the wireless charger non-radiative power transfer can occur by capacitive coupling of electric fields. However, somebody skilled in the art should be able to design numerous alternative technical solutions of a wireless charger without departing from the scope of this invention. The receiver element of the wireless charger 1808 also includes a voltage regulator circuit that interfaces with the battery module 1810. The purpose of the voltage regulator is to assure that the battery charging process is performed safely and efficiently, per battery recommended charging regime provided by the battery's manufacturer. Also, since the EM elements of the item 100 wire windings comprise a substantial number of turns made out of a very tiny copper wire, they are expected to have a significant electrical resistance. The relatively high ampere value of the electric current pulse circulating through said windings, necessary to temporarily demagnetize the magnetic assembly 100, may generate a substantial voltage differential across the EM elements wire windings terminations, due to their significant electrical resistance, as mentioned above. This voltage differential may be above the battery voltage capability. Therefore, it is necessary to interface a voltage boost converter circuit 1801 between the battery module 1810 and wire terminations 1802 and 1803 respectively. Wire terminations 1802 and 1803 are connected to the EM wire windings, so boost converter circuit 1801 can provide the regulated voltage differential that shall reliably energize the EM elements to temporary cancel the magnetic assembly attraction force. It must be mentioned that the boost circuit 1801 interfaced between the battery 1810 and the wire terminations 1802 and 1803, determines the electric current drawn from the battery module 1810 to have a higher ampere value than the electric current flowing into the EM elements wire windings. On the other hand, a battery has a limited maximum electric current capability that may not be sufficient to energize the EM elements to the necessary level. To overcome this problem, a supercapacitor may be connected in parallel with the battery, as can be observed in FIG. 18 electric diagram illustrating the item 1810 module. The supercapacitor shall be able to deliver the pulsating electric power needed by the EM elements to reliably demagnetize the magnetic assembly 100. The control & power unit 1301 also comprises a microcontroller & wireless communication unit 1806, which has multiple functions:

1. It receives the feedback signal coming from the food bolus' detection sensor via wire connection 1804. Based on this signal, item 1806 decides when to activate boost circuit 1801 to energize the magnetic assembly's EM elements.

2. It receives a thermally proportional electric signal feedback via wire connection 1805 from thermal sensors (not shown) implanted into the magnetic ring's EM elements: if the EM elements temperature increases over a certain limit due to the patient swallowing at a high frequency rate, the microcontroller shall decide to stop energizing the EM elements until their temperature decreases to an acceptable level. This feature is necessary to protect the patient and the implanted battery.

3. It can relay useful information via a wireless communication protocol (e.g. bluetooth) to the external charging & display station 1302, or to a mobile smartphone (by means of a software application designed specifically for this purpose). An example of such messages may be, but are not limited to, communicating the remaining battery charge between recharging cycles or estimated remaining battery life. In the end, it is important to mention that the battery module 1810 provides the necessary electric power to assure proper functionality of all control & power unit's electrical circuits.

Figure 19:
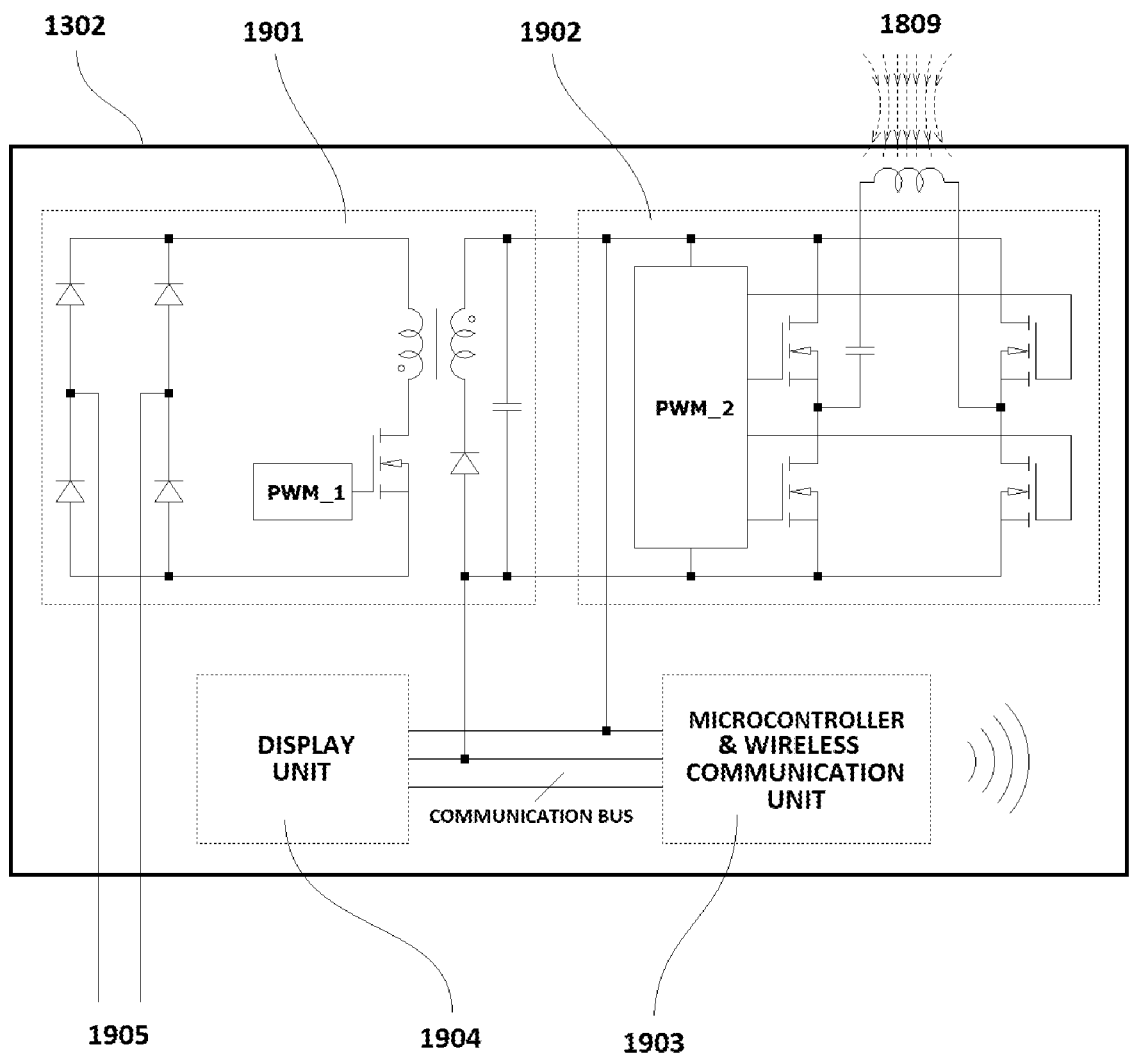
FIG. 19 is a block diagram of the Charging & Display Station (CDS).

FIG. 19 illustrates the internal block diagram of the charging & display station 1302. As it was explained in the previous paragraph, it includes the transmitter element 1902 of the wireless charger that, in combination with the implanted receiver 1808, charges the battery module 1810 via non-radiative power transfer 1809. Transmitter element 1902 gets its power from power supply 1901 which can be connected to an AC electric power wall outlet or a portable power source (e.g. bigger energy storage battery) via electrical connections 1905. Additionally, charging & display station 1302 comprises a wireless communication unit 1903 that may exchange information with the implanted counterpart (item 1806) via a wireless communication protocol 1807 (E.g. bluetooth). In turn, wireless communication unit 1903 internally sends relevant information to the display unit 1904 to make it accessible and visible to the patient, if the patient is not using an independent mobile smartphone (via the dedicated software application).

It is important to mention that the battery charging should be a convenient process that should not last more than about 15 minutes for a charging cycle. To make it effortless, the transmitter element 1902 of the charging & display station 1302 should provide a flexible cable with a termination that should incorporate the inductive coil and may include a small permanent magnet (not shown) that should "stick" to the skin area where the implanted control & power unit 1301 is located, even if the patient wears light clothes. In order to accomplish this, the implanted control & power unit 1301 should comprise a small piece of ferromagnetic material (not shown) that will be attracted by the permanent magnet located in the transmitter element extended termination 1902, when the transmitter element is brought in the proximity of the implanted control & power unit 1301. Charging and display station 1302 (and/or a mobile smartphone, if desired) should be able to show the patient the charging status in real time as it occurs.

Although it seems obvious, it must be emphasized that the exposed parts of all the implanted modules must be made of biocompatible materials. All implanted modules must not pose any safety risks while energized or non-energized including, but not limited to, electric shock, excessive temperature, and dangerous levels of radiation. Additionally, they must be free of hazardous chemical substances.

What is claimed is:

1. Apparatus for restoring the lower esophagus sphincter's (LES) normal function in human patients suffering from gastro-esophageal reflux disease comprising:
    a magnetic assembly of alternating permanent magnet elements and electromagnet elements including thermal sensors, implanted around the LES in a ring configuration;
    a control and power unit implanted under the skin in the abdominal area comprising a rechargeable battery and connected electrically to the electromagnet elements of the magnetic assembly;
    an implanted food bolus' detection sensor, attached to the esophagus in the thoracic cavity, above the LES, connected electrically to the control and power unit;
    an external display and charger station.

2. Method of transferring electric energy from control and power unit to the electromagnet elements of the magnetic assembly defined in claim 1, when food bolus approaching the LES is sensed by the food bolus' detection sensor defined in claim 1.

3. Method to temporary disable the transfer of electric energy from control and power unit to the electromagnet elements of the magnetic assembly defined in claim 1, if said electromagnet elements temperature increases above a threshold value.

4. Method to mechanically attach the permanent magnet elements to the electromagnet elements to allow the magnetic assembly defined in claim 1 to reliably expand when said electromagnet elements are briefly electrically energized by the control and power unit defined in claim 1, and to reliably contract when said electromagnet elements are not electrically energized by the said control and power unit.

5. Method of wirelessly charging the rechargeable battery included in the control and power unit defined in claim 1 by using the external display and charging station defined in claim 1.

6. Method of wirelessly communicating messages to patient, from the control and power unit defined in claim 1 by means of the display and charging station defined in claim 1.

7. Method of wirelessly communicating messages to the patient, from the control and power unit defined in claim 1 by means of a dedicated software application's mobile smartphone.

* * * * *